(12) United States Patent
Jeong et al.

(10) Patent No.: US 11,457,722 B2
(45) Date of Patent: Oct. 4, 2022

(54) SKIN CARE DEVICE

(71) Applicant: LG ELECTRONICS INC., Seoul (KR)

(72) Inventors: Hwoasu Jeong, Seoul (KR); Byungwon Cho, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 384 days.

(21) Appl. No.: 16/618,295

(22) PCT Filed: Apr. 19, 2018

(86) PCT No.: PCT/KR2018/004542
§ 371 (c)(1),
(2) Date: Nov. 29, 2019

(87) PCT Pub. No.: WO2018/236037
PCT Pub. Date: Dec. 27, 2018

(65) Prior Publication Data
US 2021/0153638 A1    May 27, 2021

(30) Foreign Application Priority Data

Jun. 19, 2017   (KR) ........................ 10-2017-0077157

(51) Int. Cl.
*A46B 13/02*   (2006.01)
*A47K 7/04*    (2006.01)
(Continued)

(52) U.S. Cl.
CPC ............ *A46B 13/02* (2013.01); *A46B 13/023* (2013.01); *A47K 7/043* (2013.01); *A61L 2/10* (2013.01);
(Continued)

(58) Field of Classification Search
CPC .................. A46B 13/02; A46B 13/023; A46B 2200/1006; A46B 2200/102; A47K 7/04; A47K 7/043; A61L 2/10
See application file for complete search history.

(56) References Cited

U.S. PATENT DOCUMENTS 9,596,928 B2   3/2017   Pardo et al.
9,717,325 B2   8/2017   Mongan et al.
(Continued)

FOREIGN PATENT DOCUMENTS

AU   2011201638 A1   3/2012
CN   202288067 U    7/2012
(Continued)

*Primary Examiner* — Randall E Chin
(74) *Attorney, Agent, or Firm* — Birch, Stewart, Kolasch & Birch, LLP

(57) ABSTRACT

Provided is a skin care device including at least one brush brought into contact with skin of a user, a motor configured to rotate or vibrate at least one of the at least one brush, a battery configured to supply power to the moto, a main body provided with the at least one brush disposed on one surface thereof and having an accommodation space configured to accommodate the motor and the battery therein, and a cradle having an accommodation space configured to accommodate the at least one brush and having a charging module configured to supply power to the battery.

9 Claims, 9 Drawing Sheets

(51) Int. Cl.
*A61L 2/10* (2006.01)
*H04R 1/02* (2006.01)

(52) U.S. Cl.
CPC . *A46B 2200/102* (2013.01); *A46B 2200/1006* (2013.01); *H04R 1/028* (2013.01)

(56) References Cited

U.S. PATENT DOCUMENTS

2015/0313354 A1* 11/2015 Mongan ................ A46B 17/06
                                                          15/105
2017/0216466 A1    8/2017 Dujowich et al.
2017/0332850 A1* 11/2017 Powell ................ A46B 13/008

FOREIGN PATENT DOCUMENTS

| CN | 105640405 A   | 6/2016 |
| CN | 205548428 U   | 9/2016 |
| CN | 105992542 A   | 10/2016 |
| CN | 106231967 A   | 12/2016 |
| CN | 106413658 A   | 2/2017 |
| CN | 106617660 A   | 5/2017 |
| JP | 2017-51588 A  | 3/2017 |
| KR | 10-2010-0088000 A | 8/2010 |
| KR | 10-2012-0026696 A | 3/2012 |
| KR | 10-2015-0099662 A | 9/2015 |
| KR | 10-1599783 B1 | 3/2016 |
| KR | 10-1649522 B1 | 8/2016 |
| KR | 10-2016-0136568 A | 11/2016 |
| WO | WO 2016/064441 A1 | 4/2016 |

* cited by examiner

| Level | Category | FOREHEAD | NOSE | JAW | LEFT CHEEK | RIGHT CHEEK |
|---|---|---|---|---|---|---|
| AUTO | Time | 20sec | 10sec | 10sec | 10sec | 10sec |
| | Left/Right motion (Inner Brush) | 200 times/sec | 200 times/sec | 200 times/sec | 100 times/sec | 100 times/sec |
| | Back/front motion (in&out Brush All) | 200 times/sec | 100 times/sec | 100 times/sec | × | × |

SKIN CARE DEVICE

CROSS REFERENCE TO RELATED APPLICATIONS

This application is the National Phase of PCT International Application No. PCT/KR2018/004542, filed on Apr. 19, 2018, which claims priority under 35 U.S.C. 119(a) to Patent Application No. 10-2017-0077157, filed in the Republic of Korea on Jun. 19, 2017, all of which are hereby expressly incorporated by reference into the present application.

BACKGROUND

The present disclosure relates to a skin care device, and more particularly, to a skin care device including a cradle for accommodating a brush of a main body and charging a battery of the main body.

Skin care is aimed at maintaining blemish-free, clean and smooth skin, and most attention is directed to skin care of a face among body parts. Therefore, people wants to keep the skin clean by getting a massage, applying a functional cosmetic product, or using various cleaning products to care for facial skin.

Here, importance of face washing to remove wastes of the skin or the like has gradually increased, for the purpose of face washing, people want to remove the wastes of the skin by applying a cleaning product to the face by hands and then rinsing the face with water.

However, in the case of face washing with hands, the cleaning product may not be evenly delivered to the skin and bacterial infection may occur due to the hand, and thus, recently, a method of indirectly applying cleaning products to the face using various tools is used. In particular, a method for washing face using a skin care device including a brush to generate vibration or rotation among the tools is gaining popularity.

However, in the case of the skin care device of the related art, bacteria may occur in the brush itself over time, and thus, continuous use of the may adversely affect the skin. In addition, there may be an optimal brush rotation or vibration speed (or intensity) depending on parts of skin but the user may not be aware of it accurately.

SUMMARY

An aspect of the present disclosure is directed to a skin care device having a cradle which may accommodate a brush of a main body and may perform sterilization on the brush at the same time.

Another aspect of the present disclosure is directed to a skin care device which may vary operations of a brush according to skin parts.

To achieve these and other advantages and in accordance with the purpose of the invention, as embodied and broadly described herein, there is provided a skin care device including: at least one brush brought into contact with skin of a user; a motor configured to rotate or vibrate at least one of the at least one brush; a battery configured to supply power to the motor; a main body provided with the at least one brush disposed on one surface thereof and having an accommodation space configured to accommodate the motor and the battery therein; and a cradle having an accommodation space configured to accommodate the at least one brush and having a charging module configured to supply power to the battery.

The cradle may further include a sterilization module configured to irradiate ultraviolet light to the at least one brush accommodated in the accommodation space.

The sterilization module may include a UV-C LED configured to irradiate ultraviolet light having a UV-C wavelength.

According to an embodiment, the cradle may further include a light diffuser disposed between the accommodation space and the sterilization module.

The cradle may further include: an upper case forming the accommodation space and configured to accommodate the light diffuser; and a lower case formed below the upper case and configured to accommodate the charging module, wherein the lower case may have at least one discharge hole allowing water to be discharged to the outside therethrough, and the at least one discharge hole may be provided along a concentric circle spaced apart from a center of the lower case.

The cradle may further include a charging module sealing portion provided between an inner circumferential surface of the upper case and an outer boundary surface of the at least one discharge hole.

According to an embodiment, the sterilization module may be disposed in an inner boundary surface of each of the at least one discharge hole, that is, at a center of the lower case, and the cradle may further include: a sterilization module sealing portion provided between a lower portion of the light diffuser and the inner boundary surface of the at least one discharge hole.

The main body may further include: a controller configured to control an operation of the motor, wherein the controller may control the motor to rotate or vibrate the at least one brush for a predetermined time when the at least one brush is accommodated in the accommodation space as the main body is mounted on the cradle, and the sterilization module may irradiate the ultraviolet light after the lapse of the predetermined time.

According to an embodiment, the at least one brush may include an inner brush and an outer brush provided outside the inner brush.

The main body may include: a connection portion rotated by driving of the motor; an inner brush fixing portion fastened to the connection portion; and an inner brush base fastened to the inner brush fixing portion and allowing the inner brush to be fixed thereto.

The main body may further include: a case forming an appearance of the main body; a cover formed on an opposite side of the one surface; and a speaker provided between the case and the cover.

According to an embodiment, the cover may be provided with a speaker hole opening a portion of the speaker to the outside, the case may be provided with a depressed portion formed by depressing a portion to an inside of the main body, and an echo space may be provided between the depressed portion and the speaker.

The main body may further include a speaker sealing member provided between the speaker and the case and configured to shield the echo space from the outside.

It is to be understood that both the foregoing general description and the following detailed description of the present disclosure are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiments of the invention and together with the description serve to explain the principle of the invention. In the drawings.

DETAILED DESCRIPTION OF THE EMBODIMENTS

Hereinafter, the embodiments of the present invention will be described with reference to the accompanying drawings, in which like numbers refer to like elements throughout although the embodiments are different, and a description of the like elements a first embodiment will be used for those of the different embodiment. In the following description, usage of suffixes such as 'module', 'part' or 'unit' used for referring to elements is given merely to facilitate explanation of the present invention, without having any significant meaning by itself. In describing the present invention, if a detailed explanation for a related known function or construction is considered to unnecessarily divert the gist of the present invention, such explanation has been omitted but would be understood by those skilled in the art. The accompanying drawings of the present invention aim to facilitate understanding of the present invention and should not be construed as limited to the accompanying drawings. Also, the present invention is not limited to a specific disclosed form, but includes all modifications, equivalents, and substitutions without departing from the scope and spirit of the present invention.

It will be understood that, although the terms first, second, etc. may be used herein to describe various elements, these elements should not be limited by these terms. These terms are only used to distinguish one element from another.

It is to be understood that when one element is referred to as being "connected to" or "coupled to" another element, it may be connected directly to or coupled directly to another element or be connected to or coupled to another element, having the other element intervening therebetween. Meanwhile, it is to be understood that when one element is referred to as being "connected directly to" or "coupled directly to" another element, it may be connected to or coupled to another element without the other element intervening therebetween.

As used herein, the singular forms "a", "an" and "the" are intended to include the plural forms as well, unless the context clearly indicates otherwise.

It will be further understood that the terms "comprises" "comprising," "includes" and/or "including" when used herein, specify the presence of stated features, integers, steps, operations, elements, and/or components, but do not preclude the presence or addition of one or more other features, steps, operations, elements, components, and/or groups thereof.

Hereinafter, embodiments of the present disclosure will be described in detail with reference to the accompanying drawings.

Figure 1:
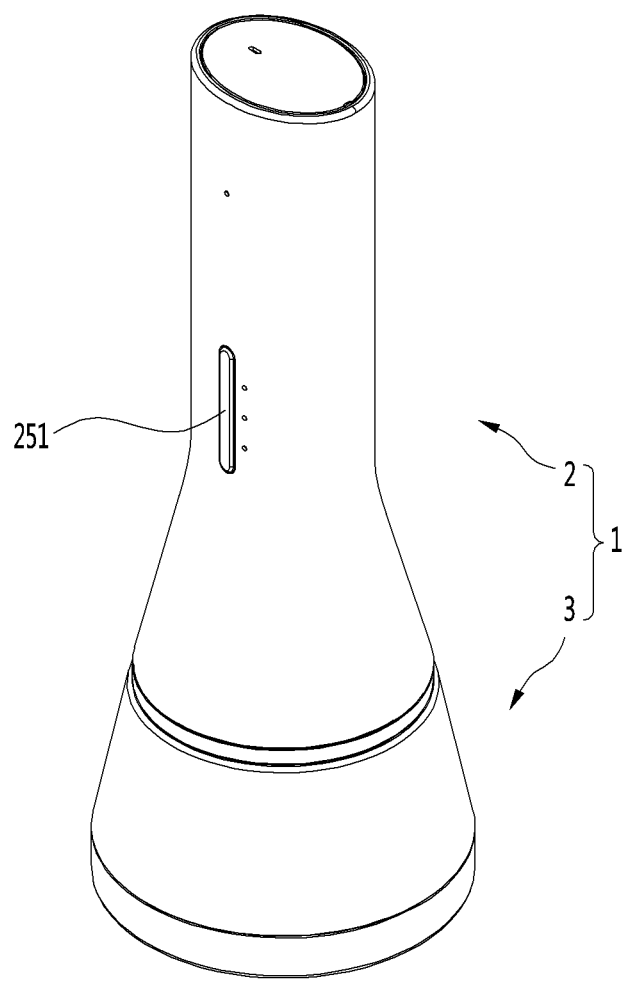
FIG. 1 is a perspective view of a skin care device according to an embodiment of the present disclosure.
Figure 2:
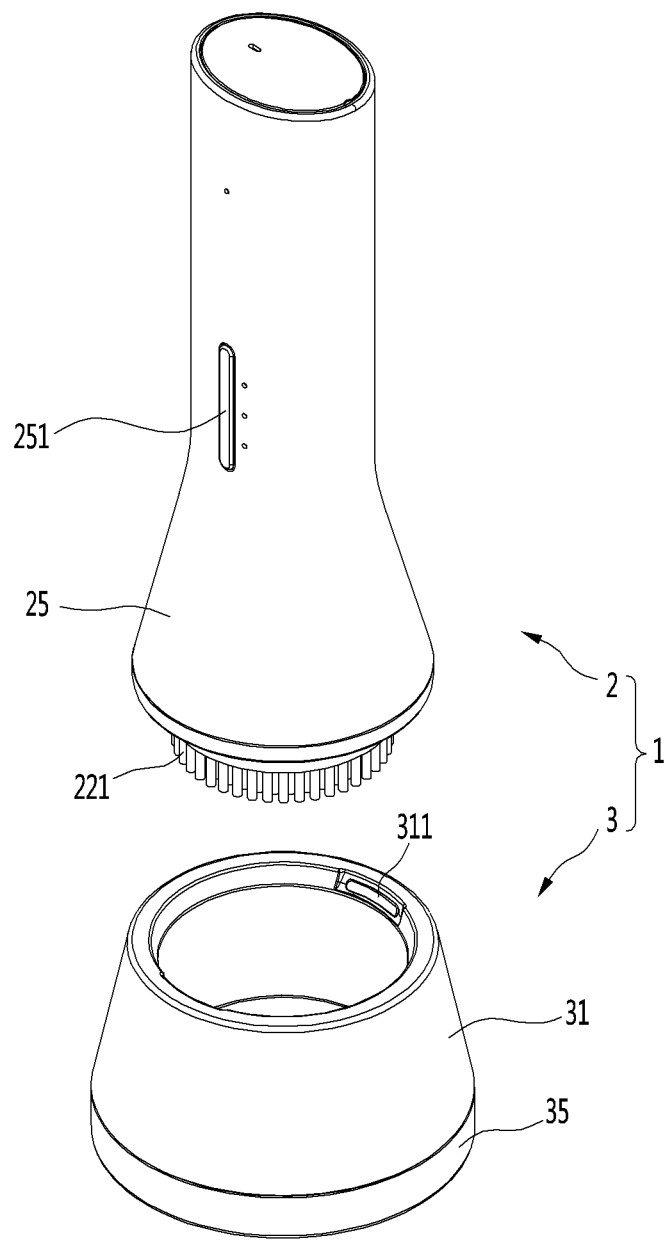
FIG. 2 is a perspective view illustrating a main body and a cradle included in a skin care device according to an embodiment of the present disclosure which are separated.

FIG. 1 is a perspective view of a skin care device according to an embodiment of the present disclosure and FIG. 2 is a perspective view when a main body and a cradle included in the skin care device according to an embodiment of the present disclosure are separated.

Referring to FIGS. 1 and 2, the skin care device 1 according to an embodiment of the present disclosure may be brought into contact with the user's skin to clean the skin or apply a certain stimulation to the skin to massage the skin. The skin care device 1 may include the body 2 and the cradle 3.

The main body 2 may have a shape allowing the user to easily grip the main body 2 and bring one end having the brushes 211 and 221 into close contact with the skin to clean or massage the skin. For example, the main body 2 may include a case 25 having at least a portion in a cylindrical shape, so that the user may easily grip the case 25 by hand.

The main body 2 may include the brushes 211 and 221 at one end thereof. As illustrated in FIG. 2, one end of the main body 2 provided with the brushes 211 and 221 may be wider than the other end of the main body 2.

The main body 2 may include a button portion 251 disposed at the case 25. An embodiment related to the button portion 251 will be described in more detail later with reference to FIGS. 9 to 10.

The cradle 3 may be connected to (or mounted at) the main body 2 to supply power for charging the battery included in the main body 2. To this end, the cradle 3 may include a cradle contact terminal 311 in contact with the main body contact terminal provided at the main body 2.

The cradle 3 may have a cylindrical shape increasing in width downward. In particular, an upper inner circumference of the cradle 3 is larger than an outer circumference of the brush 221 to accommodate the brush 221 in the cradle 3 when the body 2 is mounted on the cradle 3.

In addition, the cradle 3 according to an embodiment of the present disclosure may be provided with a sterilization module for the sterilization operation of the brushes 211 and 221 provided at the main body 2.

Hereinafter, the components provided at the main body 2 will be described with reference to FIGS. 3 to 4.

Figure 3:
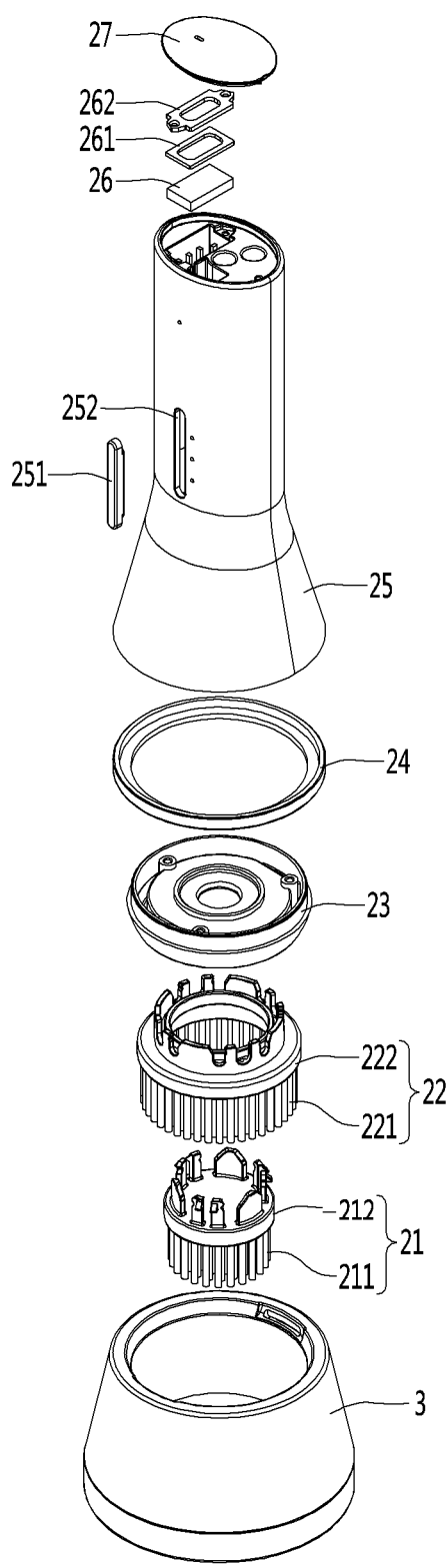
FIG. 3 is an exploded perspective view of a main body included in a skin care device according to an embodiment of the present disclosure.
Figure 4:
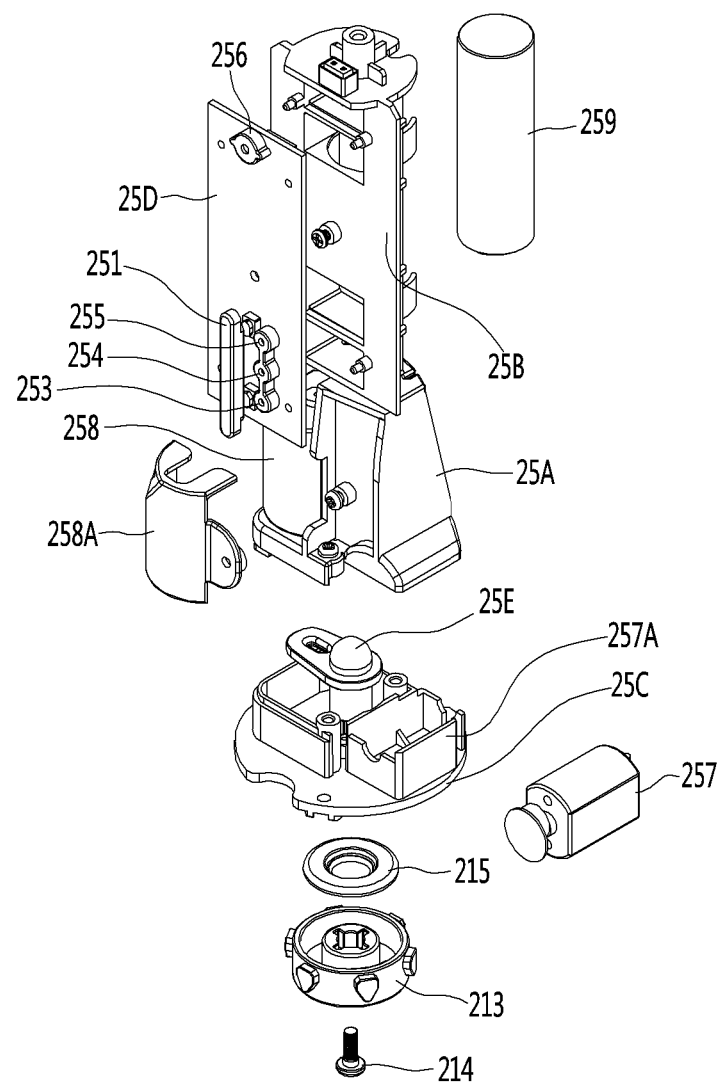
FIG. 4 is an exploded perspective view of components provided in a case of the main body illustrated in FIG. 3.

FIG. 3 is an exploded perspective view of a main body included in a skin care device according to an embodiment of the present disclosure, and FIG. 4 is an exploded perspective view of components provided in a case of the main body shown in FIG. 3.

In the drawings, a portion in which the brushes 211 and 221 of the main body 2 are disposed is defined as an upper portion, and a portion in which a speaker 26 is disposed is defined as a lower portion.

Referring to FIG. 3, the main body 2 may include an inner brush module 21, an outer brush module 22, an upper cover 23, a case 25, a speaker 26, and a lower cover 27.

The inner brush module 21 may include an inner brush 211 and an inner brush base 212, and the outer brush module 22 may include an outer brush 221 and an outer brush base 222.

The inner brush 211 and the outer brush 221 may be brought into close contact with the skin to clean the skin or massage the skin. Each of the inner brush 211 and the outer brush 221 may have a plurality of hairs. The hair provided in each of the inner brush 21 and the outer brush 221 may be formed of various materials such as plastic such as polyurethane, polyethylene, polyester, polyether, polypropylene, polystyrene, ABS, SAN, acryl, polyamide, polycarbonate, polyethylene terephthalate, and nylon or silicone, ceramic, rubber, natural fiber or artificial fiber.

The outer brush 221 may form an accommodation space accommodating the inner brush 211 therein. That is, the inner circumference of the outer brush 221 may be larger than the outer circumference of the inner brush 211.

According to an embodiment of the present disclosure, the inner brush 211 may repeat the operation of rotating at a predetermined angle in a clockwise and/or counterclockwise direction. In addition, the inner brush 211 and the outer brush 221 may vibrate up and down. That is, the outer brush 221 may vibrate up and down, without being rotated. However, in some embodiments, the outer brush 221 may also rotate. Here, the outer brush 221 may rotate in a direction opposite to the inner brush 211.

The inner brush 211 may be fixed (or attached) to the inner brush base 212, and the outer brush 221 may be fixed (or attached) to the outer brush base 222.

According to an embodiment, each of the inner brush base 212 and the outer brush base 222 may include a light emitting device for providing information on a replacement cycle of the inner brush 211 and the outer brush 221. A controller of the main body 2 may provide the user with information on whether each of the inner brush 211 and the outer brush 221 needs to be replaced through the light emitting device based on a usage time of each of the inner brush 211 and the outer brush 221.

The upper cover 23 may be formed to cover an upper portion of the main body 2. The upper cover 23 may form a space for accommodating the inner brush base 212 and the outer brush base 222 therein. In addition, a through hole may be formed at the upper cover 23 to allow a portion of a connection portion 25E to be connected to an inner brush fixing portion 213 therethrough.

Although not shown, the upper cover 23 may be provided with a main body contact terminal brought into contact with a cradle contact terminal 311 of the cradle 3 to receive power for charging the battery 259 from the cradle 3. When the main body 2 is mounted on the cradle 3 and the main body contact terminal and the cradle contact terminal 311 come into contact with each other, power from the cradle 3 may be supplied to the battery 259 through the cradle contact terminal 311 and the main body contact terminal.

The sealing member 24 may be provided between the upper cover 23 and the case 25. The sealing member 24 may seal a gap between the upper cover 23 and the case 25 to prevent water, cleaning products, or the like from penetrating into the case 25. The sealing member 24 may be formed of a material such as rubber or silicon.

The case 25 may form an outer appearance of the main body 2 and form an accommodation space that accommodates various components for the operation of the main body 2 therein. As described above with reference to FIGS. 1 and 2, at least a portion of the case 25 may have a cylindrical shape so that the user may easily grasp it by hand.

The case 25 may have a button portion 251 through groove 252 allowing the button portion 251 connected to an internal board to protrude to the outside therethrough.

The speaker 26 may be provided at a lower portion of the main body 2. The speaker 26 may output sounds such as beep, voice, and various sounds according to an operating state of the main body 2.

The lower cover 27 may be coupled to the case 25 to cover the lower portion of the main body 2 to protect various components inside the case 25. The lower cover 27 may be provided with a speaker hole for smoothly outputting sound from the speaker 26 to the outside. A portion of the speaker 26 may be opened to the outside by the speaker hole.

According to an embodiment, a speaker sealing member 261 for waterproofing the speaker 26 and a speaker fixing portion 262 for fixing the speaker 26 and the speaker sealing member 261 to the inner frame 25B in the main body 2 may be further formed between the speaker 26 and the lower cover 27.

Referring to FIG. 4, an inner brush fixing portion 213, inner frames 25A and 25B, an upper cover fixing portion 25C, a board 25D, and a connection portion 25E may be provided inside the case 25.

The inner brush fixing portion 213 may be coupled to the inner brush base 212 to rotatably and vibratably fix the inner brush module 21 to the main body 2.

The inner brush fixing portion 213 may be fastened to the connection portion 25E of the upper cover fixing portion 25C through a screw 214. According to an embodiment, a sealing member 215 may be included between the inner brush fixing portion 213 and the upper cover fixing portion 25C.

Various components inside the main body 2 may be mounted on or connected to the inner frames 25A and 25B. For example, the upper cover fixing portion 25C and the board 25D may be connected to the inner frames 25A and 25B. In addition, a rotary motor 258, a rotary motor fixing portion 258A, and a battery 259 may be mounted on the inner frames 25A and 25B.

The rotary motor 258 may provide power for a rotational operation of the inner brush module 21. When the rotary motor 258 operates, the connection portion 25E connected to the rotary motor 258 may rotate. As the connection portion 25E rotates, the inner brush fixing portion 213 fastened to the connection portion 25E and the inner brush module 21 may also rotate.

The rotary motor fixing portion 258A may fix the rotary motor 258 to the inner frame 25A, thereby preventing separation of the rotary motor 258 when the rotary motor operates.

The battery 259 may supply power for the operation of various components included in the main body 2. For example, the battery 259 may supply power required for the operation of the components provided at the board 25D and driving of the motors 257 and 258.

When the main body 2 is mounted on the cradle 3, the battery 259 may be charged by power supplied from the cradle 3.

A vibration motor accommodating portion 257A for accommodating the vibration motor 257 may be formed at the upper cover fixing portion 25C to which the upper cover 23 is fixed. The vibration motor 257 may be disposed between the vibration motor accommodating portion 257A and the inner frame 25A, so that the vibration motor 257 may be prevented from being separated when driven. The vibration motor 257 may provide power for vertical vibration of the inner brush module 21 and the outer brush module 22.

In the present disclosure, it is described that the vibration motor 257 for vibration of the inner brush module 21 and the outer brush module 22 and the rotary motor 258 for rotation of the inner brush module 21 are separately provided, but in some embodiments, the main body 2 may have a connection structure that enables the vibration and the rotation with one motor.

The board 25D may be provided with a controller for controlling an overall operation of the main body 2. The controller may be realized as an integrated circuit (IC), a microcomputer, an embedded processor, a controller, an application processor (AP), or the like.

The board 25D may include a button portion 251 for turning on/off power of the main body 2 or changing an operation level of the main body 2, operation level LEDs 253, 254, and 255 indicating an operation level, and a battery status display LED 256 indicating a battery status. This will be described in more detail later with reference to FIG. 9.

Hereinafter, the components provided in the cradle 3 will be described with reference to FIGS. 5 and 6.

Figure 5:
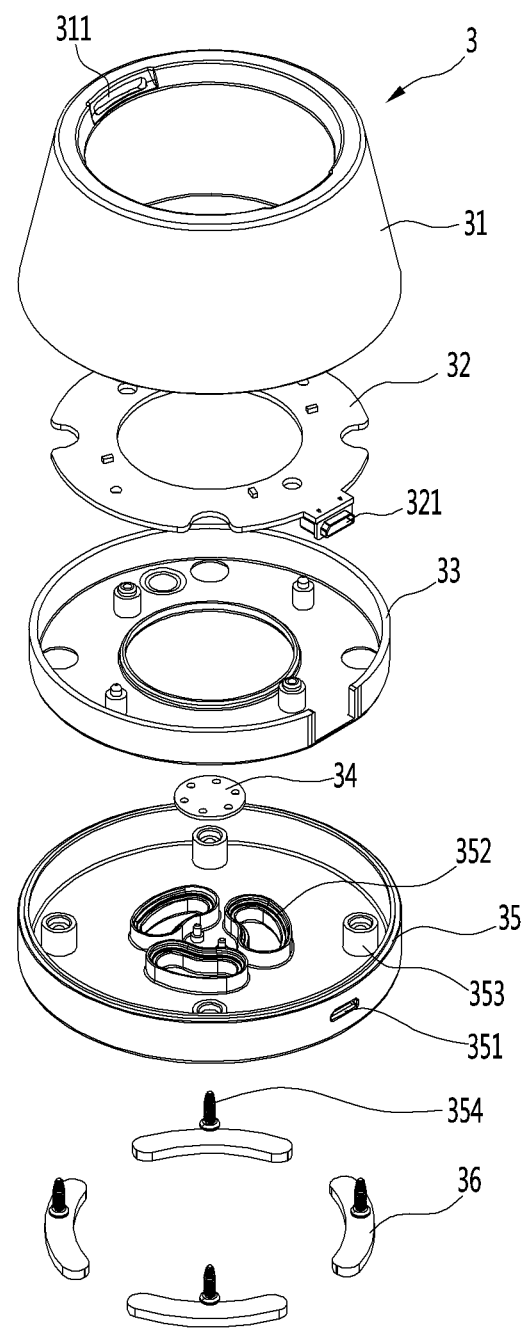
FIG. 5 is an exploded perspective view of a cradle included in a skin care device according to an embodiment of the present disclosure.

FIG. 5 is an exploded perspective view of a cradle included in the skin care device according to an embodiment of the present disclosure.

Referring to FIG. 5, the cradle 3 may include an upper case 31 and a lower case 35, and a charging module 32, an inner case 33 to which the charging module 32 is fastened, and a sterilization module 34 may be provided between the upper case 31 and the lower case 35.

The upper case 31 may form an overall appearance of the cradle 3. The upper case 31 may have an accommodation space for accommodating the inner brush 211 and the outer brush 221 of the main body 2. As described above with reference to FIGS. 1 and 2, the minimum inner circumference of the upper case 31 is formed to be larger than the outer circumference of the outer brush 221, so that the outer brush 221 may be accommodated in the upper case 31 when the main body 2 is mounted on the cradle 3.

The charging module 32 may perform an operation of supplying power to the battery of the main body 2 when the main body 2 is mounted on the cradle 3. The charging module 32 may include a power supply terminal 321 to receive power from the outside through the power supply terminal 321.

When the main body contact terminal and the cradle contact terminal 311 come into contact with each other as the main body 2 is mounted on the cradle 3, the charging module 32 may supply power supplied from the outside through the power supply terminal 321 to the battery 259 through the cradle contact terminal 311 and the main body contact terminal to thereby charge power of the battery 259. To this end, the charging module 32 may be electrically connected to the cradle contact terminal 311.

According to an embodiment, the charging module 32 may acquire information on a power state of the battery 259 and stop supplying power to the battery 259 when the battery 259 is fully charged.

The inner case 33 provided between the upper case 31 and the lower case 35 may have an accommodation space for accommodating the charging module 32 and may include a fastening portion fastened to the charging module 32. In addition, the inner case 33 may be accommodated in the lower case 35.

The sterilization module 34 may perform a sterilization operation to remove bacteria that may occur due to continuous use of the inner brush 211 and the outer brush 221. For example, the sterilization module 34 may correspond to an ultraviolet sterilization module that emits ultraviolet light to the brushes 211 and 221.

Ultraviolet (UV) light may be classified into UV-A (315-400 nm), UV-B (285-315 nm), and UV-C (200-280 nm) depending on a wavelength. For example, the sterilization module 34 may include a UV-C LED that emits light having a UV-C wavelength.

Since ultraviolet light having the UV-C wavelength cannot be visually checked by the user, it may be difficult for the user to check whether the sterilization module 34 is operating properly. According to an embodiment, the sterilization module 34 may further include an LED (not shown) that emits light of a specific color (e.g., blue). The LED may irradiate light of the specific color when the UV-C LED irradiates light having a UV-C wavelength. The user may easily check whether the sterilization module 34 is operating by checking the specific color with the naked eyes. According to an embodiment, the LED irradiating light of a specific color may irradiate light when charging of the main body 2 is completed, thereby notifying the user that charging of the battery 259 is completed.

In order for the light irradiated from the sterilization module 34 to reach the brushes 211 and 221 through the charging module 32 and the inner case 33, a light through hole may be formed at the center of the charging module 32 and the inner case 33.

The sterilization module 34 may be fixed to the lower case 35 but is not necessarily limited thereto.

The lower case 35 may accommodate the inner case 33, the charging module 32 coupled to the inner case 33, and the sterilization module 34.

The lower case 35 may include an insertion recess 351 to which an external power supply unit may be inserted so as to be connected to the power supply terminal 321. When the external power supply unit and the power supply terminal 321 are connected through the insertion recess 351, the charging module 32 may supply power supplied from the outside to the battery 259 of the main body 2. In addition, the sterilization module 34 may operate using power supplied from the outside.

The lower case 35 may further include at least one discharge hole 352 for discharging water remaining in the brushes 211 and 221 to the outside of the cradle 3. The at least one discharge hole 352 may be spaced apart from a center of the lower case 35 and the sterilization module 34 may be disposed in an inner boundary surface of the at least one discharge hole 352, that is, at the center of the lower case 35. An upper portion of the at least one discharge hole 352 may be formed to protrude through the light through hole of the charging module 32 and the inner case 33. Accordingly, water flowing out from the brushes 211 and 221 may be discharged to the outside (lower portion of the cradle 3) through the discharge hole 352 and a phenomenon that water flows to the charging module 32 or the inner case 33 may be prevented.

In order to pass through the light through hole of the charging module 32 and the inner case 33, the discharge hole 352 may be provided along a concentric circle spaced apart from the center of the lower case 35 by a predetermined distance. Here, a diameter of the concentric circle may be formed smaller than a diameter of the light through hole of the charging module 32 and the inner case 33.

The lower case 35 may be coupled to the upper case 31 through at least one fastening portion 353 and a screw 354. To this end, the inner case 33 may include at least one through hole through which the fastening portion 353 of the lower case 35 passes. In addition, at least one hole may be formed at an edge of the charging module 32, through which at least a portion of the fastening portion 353 passes.

According to an embodiment, a bottom surface of the lower case 35 may be provided with a pad 36 for suppressing horizontal movement such as sliding of the cradle 3. The pad 36 may be attached to the bottom surface of the lower case 35. The pad 36 may be formed of a material such as silicon or rubber.

Figure 6:
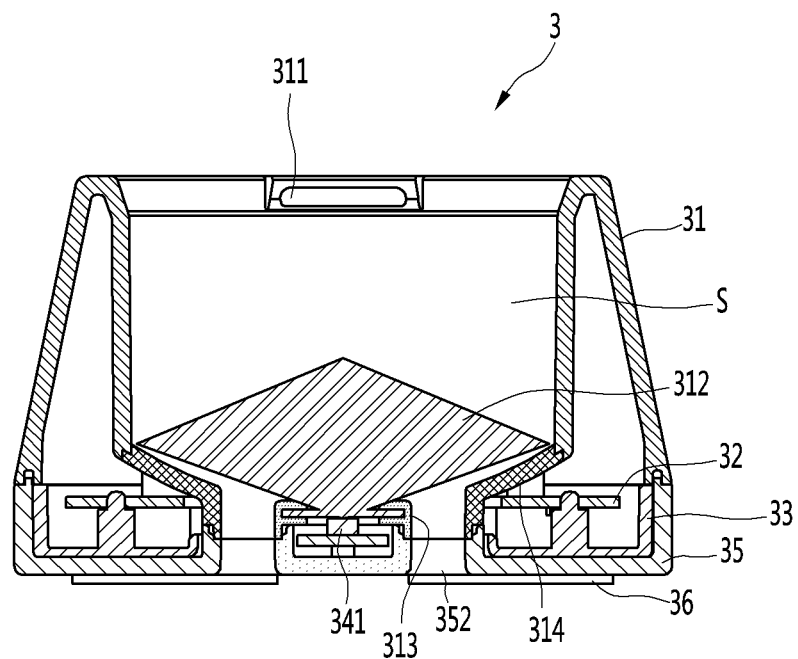
FIG. 6 is a cross-sectional view of a cradle included in a skin care device according to an embodiment of the present disclosure.

FIG. 6 is a cross-sectional view of a cradle included in a skin care device according to an embodiment of the present disclosure.

Referring to FIG. 6, the upper case 31 may have a cylindrical shape in which an outer circumference becomes wider downward and an inner circumference has a certain cylindrical shape. Accordingly, when the main body 2 is mounted on the cradle 3, the cradle 3 may stably support the main body 2 and the main body 2 may be stably mounted on the cradle 3.

The upper case 31 may include an accommodation space S for accommodating the brushes 211 and 221 when the main body 2 is mounted. As described above, the inner circumference of the upper case 31 may be larger than the outer circumference of the outer brush 221.

When the main body 2 is mounted on the cradle 3, the sterilization module 34 provided at the cradle 3 may perform sterilization operation on the brushes 211 and 221. As described above, the sterilization module 34 may include a UV-C LED 341 for irradiating light having a UV-C wavelength. Light irradiated from the UV-C LED 341 may be diffused by a light diffuser 312 and may be incident evenly onto the brushes 211 and 221.

As light having a UV-C wavelength is incident on the brushes 211 and 221, a sterilization operation may be performed on the brushes 211 and 221.

The light diffuser 312 may be disposed between the accommodation space S and the sterilization module 34. The light diffuser 312 may be formed of a transparent material such as acryl to diffuse light emitted from the UV-C LED 341 and to allow the diffused light to be incident on the brushes 211 and 221.

As shown in FIG. 6, an upper surface of the light diffuser 312 may have an inclined surface decreased in height from the center to the edge. This not only serves to disperse light having the UV-C wavelength but also water or a cleaning product flowing from the brushes 211 and 221 descend down on the inclined surface of the light diffuser 312 and is easily discharged to the outside through the discharge hole 352.

In order to prevent water or the cleaning product flowing from the brushes 211 and 221 from flowing into the sterilization module 34 along the light diffuser 312, a sterilization module sealing portion 313 may be provided under the light diffuser 312. The sterilization module sealing portion 313 may be provided between a lower portion of the light diffuser 312 and, an inner boundary surface of the discharge hole 352, thereby preventing water or the cleaning product from flowing into the sterilization module 34 disposed at the center of the lower case 35.

In addition, in order to prevent water or the cleaning product flowing from the brushes 211 and 221 from entering the charging module 32, a charging module sealing portion 314 may be provided between the inner circumferential surface of the upper case 31 and the outer diameter surface of the discharge hole 352.

The sterilization module sealing portion 313 and the charging module sealing portion 314 may be implemented with Teflon, silicon, rubber, or the like.

Figure 7:
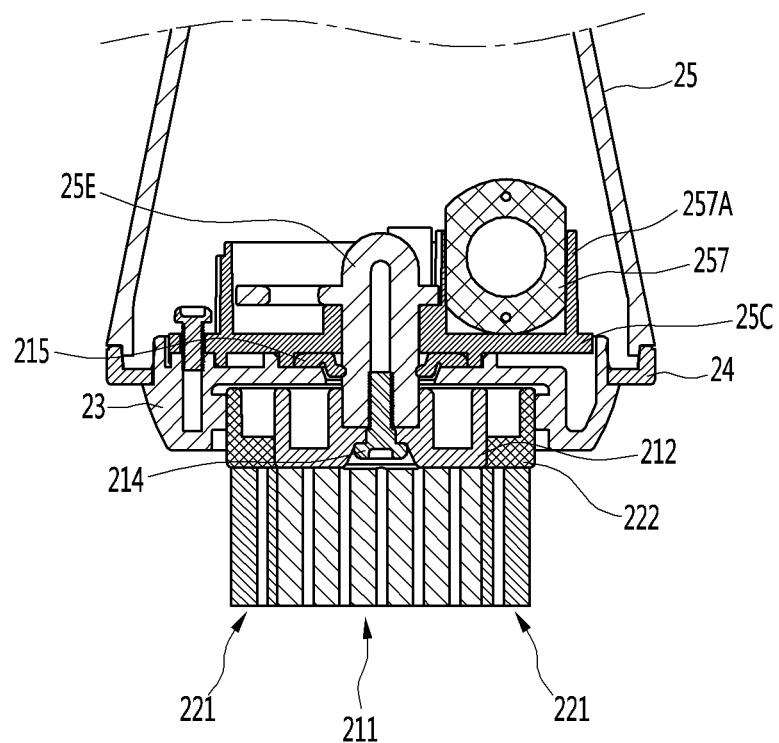
FIG. 7 is a cross-sectional view of one end where a brush is disposed among both ends of a main body of a skin care device according to an embodiment of the present disclosure.
Figure 8:
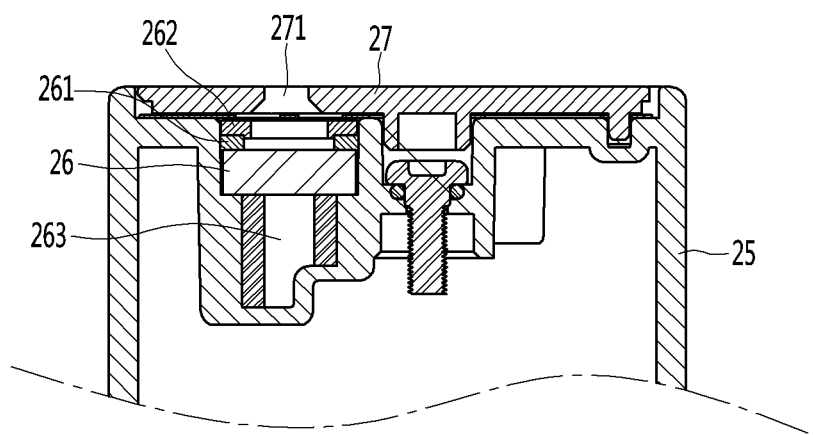
FIG. 8 is a cross-sectional view of the other end among the both ends of the main body.

FIG. 7 is a cross-sectional view of an upper portion of a main body of a skin care device according to an embodiment of the present disclosure and FIG. 8 is a cross-sectional view of a lower portion of the main body.

Referring to FIG. 7, the inner brush modules 211 and 212 and outer brush modules 221 and 222 may be provided at an upper portion of the main body 2.

The inner brush base 212 may be fastened to the inner brush fixing portion 213, and the inner brush base 212 and the inner brush fixing portion 213 may be fastened to the connection portion 25E by a screw 214. The outer brush base 222 may be connected to the inner brush base 212 or may be fastened to the upper cover 23.

A sealing member 215 may be provided between the inner brush fixing portion 213 and the connection portion 25E or between the upper cover 23 and the connection portion 25E, so that water or a cleaning product may be prevented from flowing into the main body 2 when the skin care device 1 is used.

In addition, a sealing member 24 is also provided between the upper cover 23 and the case 25 to prevent water or the cleaning product from flowing into the main body 2.

The connection portion 25E may be connected to the rotary motor 258 so as to rotate at a predetermined angle in a clockwise and counterclockwise direction based on driving of the rotary motor 258. As the connection portion 25E rotates at a predetermined angle, the inner brush base 212 and the inner brush fixing portion 213 fastened to the connection portion 25E may also rotate. As the inner brush base 212 rotates at a predetermined angle, the inner brush 211 fixed to the inner brush base 212 may also rotate to perform a washing operation on the skin part of the user.

Meanwhile, as the vibration motor 257 is driven, the connection portion 25E, the upper cover 23, or the upper cover fixing portion 25C may vibrate up and down. In this case, the inner brush base 212 and the outer brush base 222 may vibrate up and down and the inner brush 211 and the outer brush 221 may also vibrate up and down so as to come into contact with the skin of the user.

Referring to FIG. 8, a speaker 26 for outputting sound may be provided at a lower portion of the main body 2.

The speaker fixing portion 262 may be fastened to the case 25 to fix the speaker 26 to the case 25. In this case, the speaker 26 may be disposed between the case 25 and the speaker fixing portion 262. The speaker fixing portion 262 may have an opening for smoothly transmitting the sound output from the speaker 26 to the outside. An area of the opening may be equal to or larger than that of the speaker hole 271 but is not necessarily limited thereto.

An echo space 263 may be provided between the speaker 26 and the case 25. In order to form the echo space 263 while accommodating the speaker 26, the case 25 may include a depressed portion formed by depressing a portion of the main body 2. That is, an echo space 263 may be provided between the speaker 26 and the depressed portion. As the echo space 263 is formed, sound quality of the speaker 26 may be further improved.

The skin care device 1 according to an embodiment of the present disclosure is used for washing the skin area, it may frequently come into contact with water. In this case, the body 2 must be configured to prevent water from flowing into the inside thereof.

In this regard, the speaker 26 may be implemented as a waterproof speaker to minimize an influence of the inflow of water. Since the waterproof speaker corresponds to a known component, a description thereof will be omitted.

Meanwhile, if water or a cleaning product flows into the speaker fixing portion 262 through the speaker hole 271, the speaker 26 implemented as a waterproof speaker may not be affected by water. However, if water or a cleaning product flow into the echo space 263 through a gap between the speaker 26 and the case 25, sound quality of the speaker 26 may be degraded.

In order to prevent water or a cleaning product from flowing into the echo space 263, a speaker sealing member 261 may be provided between the speaker 26 and the speaker fixing portion 262 and between the speaker 26 and the case 25. may be formed. The speaker sealing member 261 may also have an opening for smoothly transmitting sound output from the speaker 26 to the outside. An area of the opening may be larger than an area of the opening formed at the speaker fixing portion 262.

The speaker sealing member 261 may be formed of rubber, silicon, or the like. Since a phenomenon in which water or a cleaning product flows into the echo space 263 is prevented by the speaker sealing member 261, sound quality of the speaker 26 may be maintained.

Figures 9, 10:
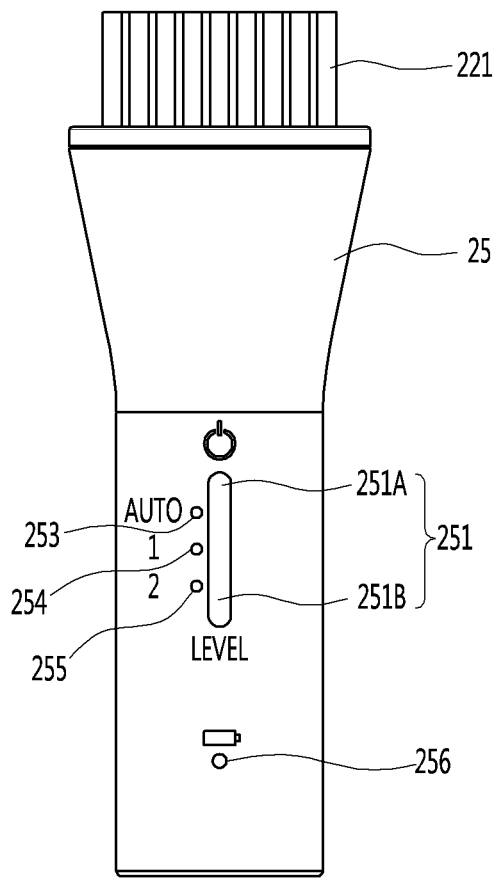
FIG. 9 is a front view of a main body included in a skin care device according to an embodiment of the present disclosure.
FIG. 10 is a view illustrating an example of an operation when a skin care device operates in the automatic mode according to an embodiment of the present disclosure.

FIG. 9 is a front view of a main body included in a skin care device according to an embodiment of the present disclosure.

Referring to FIG. 9, the button portion 251 of the main body 2 may include a power button 251A for turning on/off the main body 2 and an operation level button 251B for changing an operation level of the main body 2. As shown in FIG. 9, the power button 251A and the operation level button 251B of the button part 251 may be integrally formed, but according to an embodiment, the power button 251A and the operation level button 251B may be formed separately.

Meanwhile, the main body 2 may include operation level LEDs 253, 254, and 255 for providing a user with information on a currently selected operation level and a battery LED 256 for providing battery information of the main body 2.

Although the operation level of the main body 2 may include an auto level (automatic level), a first level, and a second level, the operation level may be further subdivided according to an embodiment. Among the operation levels, the first level may have a rotation speed or vibration speed lower than the second level. The auto level will be described later with reference to FIG. 10.

The operation level LEDs 253, 254, and 255 may include an auto level LED 253 indicating an auto level, a first level LED 254 indicating a first level, and a second level LED 255 indicating a second level. Each time the operation level button 251B is pressed, the operation level is changed and an LED corresponding to the changed operation level may be activated to emit light.

The battery LED 256 may visually provide the user with information related to a remaining capacity of the battery 259. For example, a color of the battery LED 256 may be changed or a flashing cycle or the like may be changed based on the remaining capacity of the battery 259.

For example, when the remaining capacity of the battery 259 is greater than or equal to a reference capacity, the color of the battery LED 256 may be displayed as a first color (e.g., green) or the battery LED 256 may not blink. Meanwhile, when the remaining capacity of the battery 259 is less than the reference capacity, the color of the battery LED 256 may be displayed as a second color (e.g., red) or the battery LED 256 may blink.

FIG. 10 is a view illustrating an example of an operation when the skin care device operates at an auto level according to an embodiment of the present disclosure.

Referring to FIG. 10, when the operation level of the main body 2 of the skin care device 1 is set to the auto level, the main body 2 sets different rotation speeds, vibration speeds, and usage times according to the skin parts and provide a guide for each skin area.

For example, the main body 2 may provide a guide for order for face washing so that a face washing operation may be performed in order of a forehead, a nose, a jaw, a left cheek, and the right cheek. The guide for the order of face washing may be output in the form of voice through the speaker 26. The order of face washing may be freely changed.

Referring to the order of face washing and the guide provided based on the embodiment shown in FIG. 10, when the user operates the power button 251A of the main body 2 to turn on power of the main body 2 and operates the operation level button 251B to set the operation level to the auto level, the controller of the main body 2 may output a message through the speaker 26 to guide the brushes 211 and 221 to be brought into close contact with the forehead. When the user brings the brushes 211 and 221 in close contact with the forehead in response to the message, the controller may control the vibration motor 257 and the rotary motor 258 to operate on the forehead part for a predetermined usage time at a rotational speed of the inner brush 211 and a vibration speed of the brushes 211 and 221 set for the forehead part.

When the usage time set for the forehead part elapses, the controller may output a message for instructing to bring the brushes 211, 221 to be in close contact with a nose part through the speaker 26. When the user brings the brushes 211 and 221 into close contact with the nose in response to the message, the controller may control the vibration motor 257 and the rotary motor 258 to operate on the nose part for a predetermined usage time at a rotational speed of the inner brush 211 and a vibration speed of the brushes 211 and 221 set for the nose part.

In a similar manner, the controller may output a message to perform the face washing operation in order of the jaw, the left cheek, and the right cheek, and control the vibration motor 257 and the rotary motor 258 to perform the face washing operation set according to each skin part.

According to an embodiment, the main body 2 may include a sensor (e.g., a pressure sensor or a proximity sensor) for determining whether the brushes 211 and 221 are in close contact with the skin. The sensor may be provided at the inner brush module 21 or the outer brush module 22. In this case, the controller of the main body 2 may determine whether the brushes 211 and 221 are in close contact with the skin based on information detected by the sensor.

In addition, the controller may detect the degree of adhesion between the inner brush 211 or the outer brush 221 and the skin by using the information detected by the sensor. The controller may change the rotational speed of the inner brush 211 and/or the vibration speed of the brushes 211 and 221 based on the detected degree of adhesion. For example, when the degree of adhesion is greater than a reference adhesion degree, the controller of the main body 2 may reduce the rotation speed of the inner brush 211 or reduce the vibration speed.

According to an embodiment, the controller may output a guide for a method of washing each skin part through the speaker 26. The guide may include a guide regarding a movement direction of the main body 2 according to a skin part. For example, in the case of the left cheek or the right cheek, the controller may output a guide for guiding the main body 2 to move upward from a lower side of the cheek through the speaker 26. By moving the main body 2 based on the guide, the user may wash each skin part more effectively using the skin care device 1.

In addition, the skin care device 1 may store information on an operation level frequently used based on a user's usage history and automatically sets an operation level when power of the main body 2 is turned on based on the information. In addition, the skin care device 1 may adjust a usage time, a rotational speed, and a vibration speed for each skin part at the auto level based on user information provided from a terminal such as a smartphone, a PC or the like. In this case, the skin care device 1 may further include a communication module for receiving the user information from the terminal.

Figure 11:
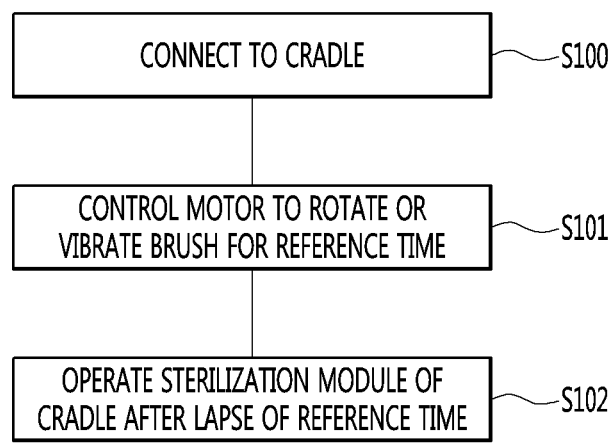
FIG. 11 is a flowchart illustrating an operation of a skin care device according to an embodiment.

FIG. 11 is a flowchart illustrating an operation of a skin care device according to an embodiment.

Referring to FIG. 11, the main body 2 of the skin care device 1 may be mounted on the cradle 3 so as to be connected to the cradle 3 (S100).

For example, the user may wash the skin using the main body 2 of the skin care device 1, and then mount the body 2 on the cradle 3. Accordingly, the main body contact terminal of the main body 2 and the cradle contact terminal 311 of the cradle 3 may come into contact with each other, whereby the main body 2 and the cradle 3 may be electrically connected.

When the main body 2 and the cradle 3 are connected to each other, the controller provided on the board 25D of the main body 2 may control the motor to rotate or vibrate the brush for a reference time (S101).

For example, moisture may remain at the inner brush 211 and the outer brush 221 of the main body 2 immediately after the use of the main body 2. When moisture remain at the inner brush 211 and the outer brush 221, sterilization efficiency may be slightly lowered. Accordingly, when the controller of the main body 2 detects contact between the main body contact terminal and the cradle contact terminal 311, the controller may rotate the vibration motor 257 and/or rotary motor 258 for a reference time to remove moisture remaining at the inner brush 211 and/or the outer brush 221. As the vibration motor 257 and/or the rotary motor 258 are driven, the inner brush 211 may rotate or the inner brush 211 and the outer brush 221 may vibrate. Moisture remaining at the brush may be effectively removed according to the rotation and/or vibration of the brush.

According to an embodiment of the present disclosure, when the brush is rotated and/or vibrated, the controller of the main body 2 may notify the user in a voice form that the removal of moisture of the brushes 211 and 221 is in progress through the speaker 26.

After the reference time has elapsed, the sterilization module 34 of the cradle 3 may perform a sterilization operation on the inner brush 211 and the outer brush 221 (S102).

The sterilization module 34 may perform a sterilization operation on the brushes 211 and 221 by controlling the UV-C LED to irradiate light having a UV-C wavelength after the reference time elapses. For example, the sterilization operation may be performed for about 40 seconds to 1 minute, but is not necessarily limited thereto. According to an embodiment, the controller of the main body 2 may output a voice indicating that the sterilization operation is performed through the speaker 26.

That is, the sterilization module 34 of the cradle 3 may be configured to operate after the lapse of the reference time from a time point when mounting of the main body 2 is detected. Accordingly, after moisture remaining at the inner brush 211 and the outer brush 221 of the main body 2 is removed to some extent, the sterilization operation may be performed, and thus, sterilization efficiency may be further improved.

According to an embodiment of the present disclosure, the cradle for accommodating the brush when the main body is mounted includes the sterilization module for sterilizing the brush, thereby minimizing a possibility of adversely affecting the user's skin by maintaining cleanness of the brush and enhancing safety of the skin care device.

Furthermore, the cradle includes a discharge hole for discharging water or a cleaning product flowing from the brush to the outside, so that the water or cleaning product is smoothly discharged to the outside without pooling in the cradle, thereby maintaining cleanness of the cradle.

Furthermore, the cradle may include a sealing portion to protect the charging module and the sterilization module from water or cleaning products, thereby preventing damage or failure of the charging module or the sterilization module.

Furthermore, when the main body is mounted at the cradle, the controller of the main body may rotate or vibrate the brush for a predetermined time to remove moisture of the brush, thereby increasing sterilization efficiency during an operation of the sterilization module.

Furthermore, the main body may improve sound quality of the speaker by forming an echo space between the case and the speaker and prevent deterioration of sound quality of the speaker due to introduction of water by providing a speaker sealing member for shielding the echo space.

Although a few embodiments have been shown and described, it will be appreciated by those skilled in the art that changes may be made in these embodiments without departing from the principles and spirit of the invention, the range of which is defined in the appended claims and their equivalents.

Accordingly, the embodiments of the present invention are provided to explain the technical spirit of the present invention but not to limit such spirit, and the scope of the technical spirit of the present invention is not limited by the embodiments of the present invention.

The scope of protection of the present invention should be interpreted by the claims below, and all technical spirits which are in the same scope would be interpreted as being included in the scope of right of the present invention.

What is claimed is:
1. A skin care device comprising:
 at least one brush brought into contact with skin of a user;
 a motor configured to rotate or vibrate at least one of the at least one brush;
 a battery configured to supply power to the motor;
 a main body provided with the at least one brush disposed on one surface thereof and having an accommodation space accommodating the motor and the battery therein; and
 a cradle including:

an accommodation space accommodating the at least one brush and having a charging module configured to supply power to the battery;
a sterilization module configured to irradiate ultraviolet light to the at least one brush accommodated in the accommodation space of the cradle;
a light diffuser disposed between the accommodation space of the cradle and the sterilization module;
an upper case forming the accommodation space of the cradle and configured to accommodate the light diffuser; and
a lower case formed below the upper case and configured to accommodate the charging module,
wherein the lower case has at least one discharge hole allowing water to be discharged to the outside therethrough, and the at least one discharge hole is provided along a concentric circle spaced apart from a center of the lower case,
wherein the sterilization module is disposed in an inner boundary surface of each of the at least one discharge hole, and
wherein the cradle further comprises a sterilization module sealing portion provided between a lower portion of the light diffuser and the inner boundary surface of each of the at least one discharge hole.

2. The skin care device of claim 1, wherein the sterilization module comprises a ultraviolet (UV)-C light emitting diode (LED) configured to irradiate ultraviolet light having a UV-C wavelength.

3. The skin care device of claim 1, wherein the cradle further comprises a charging module sealing portion provided between an inner circumferential surface of the upper case and an outer boundary surface of the at least one discharge hole.

4. The skin care device of claim 1, wherein the main body further comprises a controller configured to control an operation of the motor,
wherein the controller is configured to control the motor to rotate or vibrate the at least one brush for a predetermined time when the at least one brush is accommodated in the accommodation space of the cradle as the main body is mounted on the cradle, and
wherein the sterilization module irradiates the ultraviolet light after the lapse of the predetermined time.

5. The skin care device of claim 1, wherein the at least one brush comprises:
an inner brush; and
an outer brush provided outside the inner brush.

6. The skin care device of claim 5, wherein the main body comprises:
a connection portion rotated by driving of the motor;
an inner brush fixing portion fastened to the connection portion; and
an inner brush base fastened to the inner brush fixing portion and allowing the inner brush to be fixed thereto.

7. The skin care device of claim 1, wherein the main body further comprises:
a case forming an appearance of the main body;
a cover formed on an opposite side of the one surface; and
a speaker provided between the case and the cover.

8. The skin care device of claim 7, wherein:
the cover is provided with a speaker hole opening a portion of the speaker to the outside,
the case is provided with a depressed portion formed by depressing a portion to an inside of the main body, and
an echo space is provided between the depressed portion and the speaker.

9. A skin care device comprising:
at least one brush brought into contact with skin of a user;
a motor configured to rotate or vibrate at least one of the at least one brush;
a battery configured to supply power to the motor;
a main body provided with the at least one brush disposed on one surface thereof and having an accommodation space accommodating the motor and the battery therein; and
a cradle having an accommodation space accommodating the at least one brush and having a charging module configured to supply power to the battery,
wherein the main body further comprises:
a case forming an appearance of the main body;
a cover formed on an opposite side of the one surface; and
a speaker provided between the case and the cover,
wherein the cover is provided with a speaker hole opening a portion of the speaker to the outside,
wherein the case is provided with a depressed portion formed by depressing a portion to an inside of the main body, and
wherein an echo space is provided between the depressed portion and the speaker, and
wherein the main body further comprises a speaker sealing member provided between the speaker and the case and configured to shield the echo space from the outside.

* * * * *